United States Patent [19]

McRae

[11] Plant 4,181

[45] Jan. 3, 1978

[54] LILY PLANT LILIUM 'DAYSPRING'

[75] Inventor: Edward A. McRae, Boring, Oreg.

[73] Assignee: Melridge, Inc., Gresham, Oreg.

[21] Appl. No.: 761,233

[22] Filed: Jan. 21, 1977

[51] Int. Cl.[2] ..... A01H 5/00

[52] U.S. Cl. ..... Plt./68

[58] Field of Search ..... Plt./68

*Primary Examiner*—Robert E. Bagwill

*Attorney, Agent, or Firm*—Eugene D. Farley

[57] ABSTRACT

A new variety of Asiatic hybrid lily plant of single stem, erect and stately form, and medium height; having full foliage of lanceolate dark green leaves of glossy and leathery texture; having a high bud count; and having distinctive, upright lemon yellow flowers with gold centers and light spotting at the base; the plant being highly resistant to disease, and the bulbs being especially suitable for forcing for the production of cut flowers.

1 Drawing Figure

BACKGROUND OF THE INVENTION

My new variety of lily plant originated as a seedling selected from a group of seedlings at Gresham, Oreg. The seedlings were planted as part of a lily breeding program carried on by me since the year 1964. This program had as its main objective the production of upright Asiatic hybrid lilies having a yellow color, being highly resistant to disease and tolerant to virus, having a high bud count and flowers of a pleasing yellow tone, and generally suitable for the cut flower-forcing trade.

I achieved the desired objective by using as the seed parent a second generation ($F_2$) Lilium hybrid from the cross ('Mega' × 'Lemon Queen') × 'Edith Cecilia'. The pollen parent was *Lilium 'Croesus'*.

My new lily plant has an erect and stately form. It has a strong single stem of medium height. It grows vigorously.

The foliage of my new plant is full and comprises lanceolate leaves dark green in color and 2 to 3 inches long.

The inflorescence of my new lily plant is particularly outstanding, the flower placement and form being almost perfect. The bud count is high and the flower color highly pleasing. The color of the buds when the tepals first divide and begin to unfurl is lemon yellow with a gold center. The color of the mature flowers is a slightly deepened lemon yellow with golden midribs; the center half of each tepal is lightly spotted with medium-sized magenta to brown spots.

My new lily plant is also characterized by the desirable qualities of being highly resistant to disease, tolerant to virus, and subject to propagation by forcing precooled bulbs thereby rendering it well suited for application to the production of potted plants and cut flowers, all as observed at Gresham, Oreg.

My new variety of lily plant has been asexually reproduced by me and under my direction at Gresham, Oreg. Successive generations produced by bulb scale propagation and natural propagation from bulblets have demonstrated that the novel and distinctive characteristics of my new variety are fixed and hold true under asexual propagation from generation to generation.

DESCRIPTION OF THE DRAWING

My new variety of lily plant is illustrated in the accompanying photographic drawing which shows in full color the plant, the foliage, the buds in various stages of development and the fully opened flowers. It illustrates further the bud and flower form, the connection of the buds and flowers to the stem, and in particular the distinctive bright lemon yellow with gold center color tone of both the flowers and the ready-to-open buds.

DESCRIPTION OF THE NEW VARIETY

The following is a detailed description of my new variety of Asiatic hybrid lily, with nomenclature according to *The International Lily Register* (Royal Horticultural Society, London, 2nd Edition, 1969), and with color designations according to the Royal Horticultural Society Colour Chart, published by the R.H.S. in 1966.

THE PLANT

Origin: Seedling.

Parentage:

*Seed parent.*—(( ('Mega' × 'Lemon Queen') × 'Edith Cecilia')) $F_2$.

*Pollen parent.*—*Lilium X 'Croesus'* (unpatented).

Classification:

*Botanic.*—Hybrid Lilium clone; Division I-A of Horticultural Classification of Lilies of the R.H.S.

*Commercial.*—Asiatic hybrid lily.

Form: Single stem, erect and stately.

Height: 25 to 30 inches, when produced from bulbs 5 to 7 inches in circumference.

Growth: Vigorous, sturdy and upright.

Strength: Excellent.

Foliage:

*Quantity.*—Full.

*Size of leaf.*—3 to 4 inches long.

*Shape of leaf.*—Lanceolate.

*Texture.*—Leathery and glossy.

*Color.*—Dark green on both upper and under sides.

Bulbs:

*Size.*—Any size, ranging up to 10 inches in circumference.

*Color.*—White.

THE BUD

Form: Long, ovoid and pointed.

Size: About 2 inches long and 1 inch in circumference, increasing as bud develops.

Opening: Bud opens slowly.

Color: Lemon yellow with gold center and light spotting when tepals first divide and also when petals begin to unfurl.

Tepals: Curl back; lemon yellow with gold center and light spotting on the inside; lemon yellow on the outside.

Peduncle: About 2 inches long; erect; light green in color.

THE FLOWER

Blooming habit: Recurrent; blooms once and profusely in early summer.

Size: Medium; about 5 inches in diameter.

Borne: In clusters, from 6 to 12 on a single stem, with few secondary buds.

Shape: Flat, with tepals curling backwardly as bloom matures. Tepals are slightly frilled when flower first opens.

Tepalage:

*Number of tepals.*—6.

*Arrangement.*—Imbricated.

*Color.*—Soft lemon yellow R.H.S. C.C.12C on outer tepal, inside tepal, and on the reverse sides of the tepals and gold flush R.H.S. C.C.13A in the inside tepal centers and mid-ribs.

*Tepal longevity.*—Tepals stay on stem about 3 weeks.

*Spotting.*—Light spotting at the bases of the tepals.

Pedicel:

*Length.*—2 to 3 inches.

*Color.*—Bright green.

*Form.*—Sturdy and upright.

Color change: Color intensifies with age after full bloom.

Texture: The flower is soft.

Appearance: The flower is shiny.

Disease resistance: The flower and plant are resistant to disease; in particular, they are resistant to Fusarium and Botrytis.

Fragrance: The flower is not fragrant.

Lasting quality: The flower is long lasting both on the plant and as a cut flower.

THE REPRODUCTIVE ORGANS

Stamens, anthers:

*Arrangement.*—Typical of Liliaceae.

*Length.*—2 inches.

*Number.*—6.

*Filaments.*—About 2 inches in length; color, soft cream to yellow.

Pollen and anthers: Cinnamon brown in color.

Pistils: One in number with a length of about 2 inches.

Stigma: Purple in color.

Characteristics of ovaries: Typical of genus Lilium.

FRUIT

Fertility: The fruit is fertile.

Shape: The fruit is ovoid in shape.

Color at maturity: The fruit is soft brown.

My new lily is unique in its class and does not closely resemble any other known lily.

I claim:

1. A new and distinctive variety of Asiatic hybrid lily plant substantially as herein shown and described, characterized by its erect and stately form, its vigorous growth, its full foliage of lanceolate dark green leaves, its excellent inflorescence, its high count of buds which turn lemon yellow as the tepals first divide and begin to unfurl, its flowers comprising tepals soft lemon yellow at the tips and gold with light spotting in the centers, its high resistance to disease, its high tolerance to virus, its vigorous growth and propagation characteristics, and its suitability for propagation by forcing precooled bulbs in the production of potted plants and cut flowers.

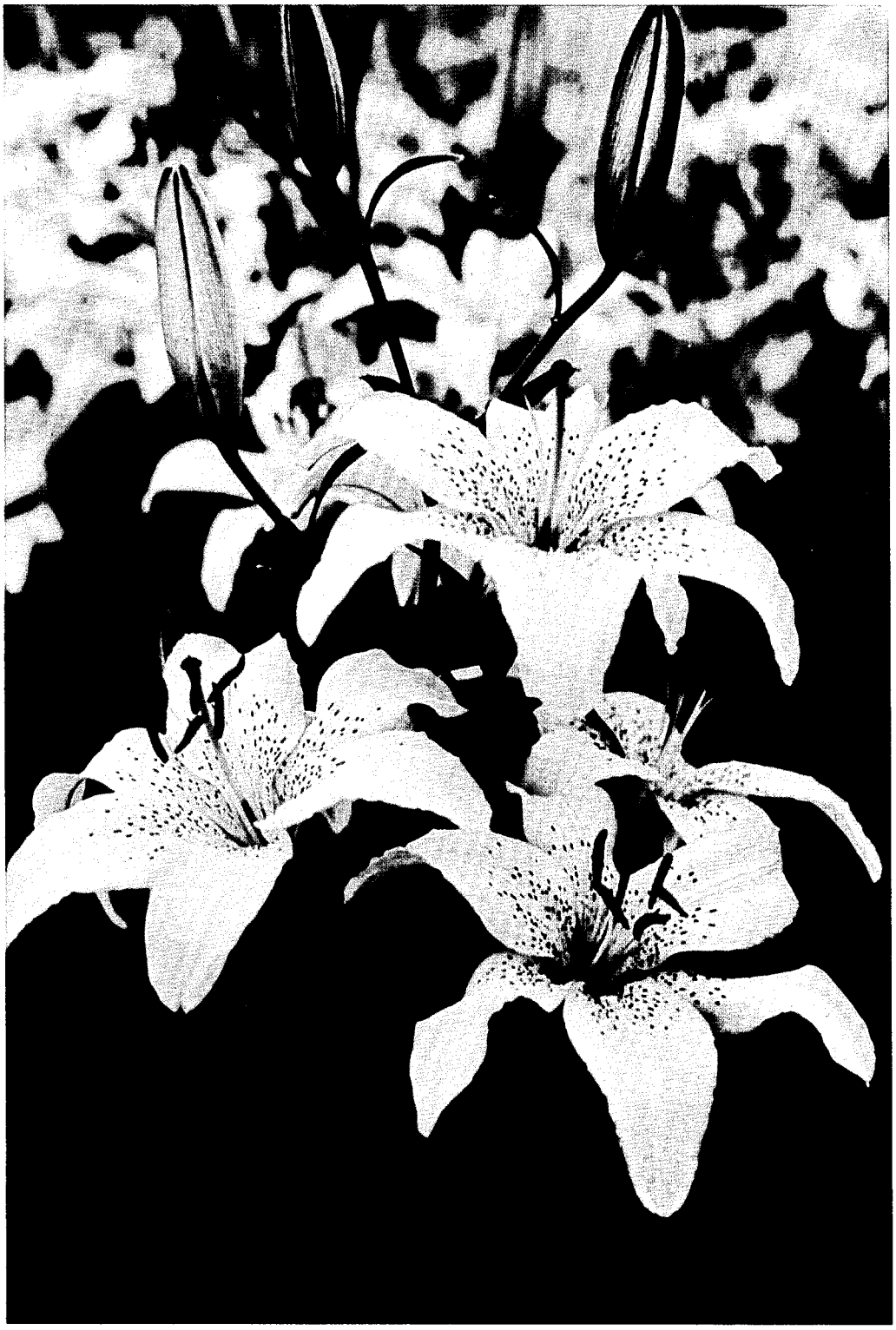

* * * * *